US005459162A

United States Patent [19]
Saxton

[11] Patent Number: 5,459,162
[45] Date of Patent: Oct. 17, 1995

[54] METHOD AND COMPOSITION FOR IMPROVING THE WEIGHT GAIN OF POULTRY

[75] Inventor: Gary B. Saxton, Houston, Tex.

[73] Assignee: Griffin Corporation, Valdosta, Ga.

[21] Appl. No.: 291,448

[22] Filed: Aug. 17, 1994

[51] Int. Cl.$^6$ .......................... A61K 31/30; A61K 33/34
[52] U.S. Cl. ............................................ 514/499; 424/630
[58] Field of Search ............................. 424/630; 514/499

[56] References Cited

U.S. PATENT DOCUMENTS

| | | | |
|---|---|---|---|
| 3,231,466 | 1/1966 | Hoffman et al. | 424/329 |
| 3,916,027 | 10/1975 | Taylor | 424/329 |
| 4,326,523 | 4/1982 | Wolfrom et al. | 128/260 |
| 4,956,188 | 9/1990 | Anderson | 426/74 |

*Primary Examiner*—Raymond Henley, III
*Assistant Examiner*—Keith MacMillan
*Attorney, Agent, or Firm*—Jones & Askew

[57] ABSTRACT

There is disclosed an improved composition and method for improving the weight gain of poultry. The improved method comprises administering orally to poultry an effective amount of copper citrate. The improved composition comprises a feed for the poultry and an effective amount of copper citrate.

13 Claims, No Drawings

METHOD AND COMPOSITION FOR IMPROVING THE WEIGHT GAIN OF POULTRY

FIELD OF THE INVENTION

The present invention relates generally to mineral feed supplements for poultry, and, more specifically, to a copper feed supplement for chickens. The present invention also relates to a method of increasing the weight gain of poultry, such as chickens, using a copper feed supplement.

BACKGROUND OF THE INVENTION

It is known in the art to treat chickens with copper in order to improve their weight gain and to prevent nutritional anemia. The copper requirements of chickens is described in M. O. North and D. D. Bell, "Commercial Chick Production Manual," Chapman & Hall, p. 599, 4th Ed., 1990, as follows:

> Nutritional anemia occurs when there are deficiencies of copper and iron in poultry's diet. The red blood cells contain iron. The mineral also is needed to pigment the feathers of certain breeds of chickens. Copper is necessary for iron utilization when hemoglobin is formed; therefore, if absent from the diet, anemia results. The amount of iron and copper needed in the diet of the chicken is quite specific; excess may be toxic. About five to ten times as much iron as copper is required. Usually, only small amounts, if any, are ever added to the feed formula.

Generally, copper sulfate is administered to the chickens by mixing or dry blending it in with their daily feed, which typically comprises corn and soybean meal. A typical prior art chicken feed with blended copper sulfate is prepared by dry blending one to two pounds of copper sulfate with one ton of chicken feed. The copper sulfate is therefore administered to the chickens at a rate of 125 ppm –250 ppm copper metal equivalent.

Although the copper sulfate produces improved weight gain in chickens compared to untreated chickens, any further improvement would be of tremendous value to the poultry industry. Furthermore, the copper in the copper sulfate is excreted by the chickens in their feces. This produces a significant disposal problem for chicken ranchers.

U.S. Pat. No. 3,231,466 relates to a composition for treating animals, including poultry. This patent discloses that the composition enhances the growth response and/or the general health of domesticated animals. The composition comprises iodine in an organic form, either choline iodine or ethylene dihydroiodide; phthalylsulfacetamide; and iron, cobalt and copper in the form of choline citrate complexes. The patent further discloses that:

> Iron is not fully utilized, however, without available copper and cobalt. For these reasons copper sulfate and cobalt sulfate became pans of the original composition. It has subsequently been determined through continuing research that the choline citrate compounds of copper and cobalt are far more desirable in that they are less toxic, more readily available, and therefore, serve more adequately to enhance absorption and utilization of the iron than do the inorganic compounds, thereby greatly stimulating hemoglobin rise and increased red blood cell counts.

Although this patent discloses copper choline citrate, it is apparent that the focus of the invention was on the addition of choline to the composition; not the addition of copper in a citrate form.

Choline is known to be an aid to the growth of chickens. As disclosed by M. O. North and D. D. Bell, "Commercial Chick Production Manual," Chapman & Hall, p. 599, 4th Ed., 1990:

> The chick's demand for choline is great. Choline forms a part of the phospholipid, lecithin, rather than an enzyme. Therefore, choline is seldom considered a true vitamin. At times it may be synthesized by the chick, but the amounts are small and usually inadequate. The older a bird gets, the better the synthesis.
>
> The vitamin has a great many functions in the body: It helps in fat movement in the bloodstream; it has a sparing action on methionine; it aids in growth; it prevents a type of slipped tendon; and it helps to reduce excessive fat deposits in the liver.

In view of this prior art, one would expect that the removal of the choline from the copper choline citrate complex would not produce an improvement in the growth of poultry.

Therefore, a need exists for a feed supplement which produces less toxic waste while maintaining or improving the weight gain of chickens treated therewith. Furthermore, there is also a need for a form of copper which enhances the growth response of poultry, but which does not include choline as a complex with copper.

SUMMARY OF THE INVENTION

The present invention satisfies the above-described needs by providing an improved poultry feed supplement and an improved method of increasing the growth response and/or weight gain in poultry. The improved method of the present invention comprises the step of administering orally to poultry an effective amount of copper citrate. The improved composition of the present invention comprises a poultry feed mixed with an effective amount of copper citrate.

Accordingly, it is an object of the present invention to provide an improved composition and an improved method for enhancing weight gain in poultry, namely, chickens.

Another object of the present invention is to provide a composition and method which enhances weight gain in poultry at lower levels of copper.

A further object of the present invention is to provide a composition and method of enhancing weight gain in poultry which is less polluting to the environment.

Yet another object of the present invention is to provide a composition for and method of treating poultry which causes the poultry to more efficiently convert their feed to body weight.

These and other objects, features and advantages of the present invention will become apparent after a review of the following detailed description of the disclosed embodiments and the appended drawing and claims.

DETAILED DESCRIPTION OF THE DISCLOSED EMBODIMENTS

The present invention relates to an improved composition and to an improved method for producing weight gain in poultry, such as chickens, turkeys, ducks, or geese. The novel method of the present invention comprises the steps of administering orally to the poultry an effective amount of copper citrate.

Copper citrate has the chemical formula $C_6H_4Cu_2O_7$.

Copper citrate is prepared by reacting either copper carbonate— $Cu_2(OH)_2CO_3$—or copper hydroxide—$Cu(OH)_2$—with citric acid— $C_6H_8O_7$. Copper citrate can also be prepared by reacting sodium citrate (trisodium citrate)—$C_6H_5O_7Na_3 \cdot 2H_2O$—with copper sulfate—$CuSO_4$. The resulting reaction produces copper citrate and in an aqueous medium. The copper citrate, which is a solid, will precipitate from the aqueous phase and can be separated by simple filtration and drying. Copper citrate is also available from several commercial sources, such as Weinstein Chemicals, Inc. of Costa Mesa, Calif.

In accordance with the present invention, it has been discovered that copper citrate will produce the same, or greater, weight gain in poultry as copper sulfate, but at approximately one-half the dose of copper metal equivalent as copper sulfate. In the prior art, copper sulfate has typically been administered to chickens at a rate of 125 ppm to 250 ppm copper metal equivalent. However, in accordance with the present invention, it has been discovered that the same, or better, results can be accomplished by treating poultry with copper citrate at a rate of approximately 50 ppm to 125 ppm copper metal equivalent; preferably, 63 ppm copper metal equivalent.

The particular poultry feeds which are useful in the present invention are not critical. Generally, those feeds which have been used in the prior art to feed poultry, particularly chickens, are suitable for use in the present invention. Typical poultry feeds which are useful in the present invention are disclosed in M. O. North and D. D. Bell, "Commercial Chick Production Manual," Chapman & Hall, 4th Ed., 1990, and may contain mixtures of the following: carbohydrates, such as, barley; buckwheat; cassava; corn, for example, yellow corn, white corn and high-lysine corn; millet (proso); molasses; oats; rice; rye; sorghums, for example, kafir and milo; triticale; and wheat; mill by-products, such as, hominy feed; rice bran; rice hulls; wheat by-products, for example, wheat bran and wheat millings, shorts; fats and oils, such as, hard fats from slaughtered cattle; soft fats, for example, yellow grease; hydrolyzed animal fats; vegetable oils; and polyunsaturated fatty acids in egg yolks; proteins of animal origin, such as, dried blood; dried poultry waste, for example, dried cage layer manure; liver meal; meat by-products, for example, meat scraps and meat and bone meal; milk products, such as, dried skim milk; dried butter milk, and dried whey; poultry by-products, such as, hydrolyzed poultry feather meal; poultry hatchery by-product meal, for example, eggshells, unhatched and infertile eggs, and culled chicks; proteins of fish origin, such as, white fish meal; dark fish meal; and shrimp meal; proteins of vegetable origin, such as, corn gluten, coconut (copra) oil meal; cottonseed meal; guar meal; linseed (flax) oil meal; peanut (groundnut) meal; rapeseed oil meal (canola meal); safflower meal; sesame meal; soybean meal; full-fat soybeans; and sunflower seed meal; green leafy products, such as, alfalfa products, for example, sun-cured alfalfa meal, dehydrated alfalfa meal, and dehydrated alfalfa leaf meal; macrominerals, such as, curacau (island) rock phosphate $(CaHPO_4)(CaHPO_4 \cdot H_2O)$; dicalcium phosphate $(CaHPO_4 \cdot 2H_2O)$; rock phosphate; steamed bone meal $(Ca_3(PO_4)_2)$; argonite $(CaCO_3)$; limestone $(CaCO_3)$; oyster shell $(CaCO_3)$; gypsum $(CaSO_4 \cdot 2H_2O)$ and salt (NaCl); and vitamins, minerals and trace ingredient, such as, fat-soluble vitamins, for example, vitamins A, D, E, and K; water-soluble vitamins, for example, C (ascorbic acid), thiamin ($B_1$), riboflavin ($B_2$), pantothenic acid, niacin, pyridoxine ($B_6$), choline, biotin, folacin (folic acid), $B_{12}$ (cobalamin); minerals, such as, calcium; phosphorus; vitamin D; sodium; chlorine; potassium; sulfur; iodine; fluorine; iron; copper; manganese; magnesium; selenium; vanadium; and zinc; amino acids, such as, methionine; cystine; lysine; tryptophan; and arginine; and other feed constituents, such as, antibiotics; arsenicals; xanthophylls; antioxidants; coccidiostat; electrolytes; pellet binders; tranquilizers and other supplements, for example, flavoring agents, enzymes, thyroactive compounds, and drugs.

A copper citrate formulation in accordance with the present invention may be produced in accordance with the present invention by the following steps. Poultry feed, such as a chicken feed, comprising ground corn and soy bean meal, is dry blended with copper citrate in powder form so that the copper titrate is uniformly distributed throughout the chicken feed. Apparatus for dry blending such components is well known to those skilled in the art. The poultry feed containing the blended copper citrate is then fed to poultry, such as chickens, so that the copper citrate is consumed by the poultry orally along with the poultry feed.

There is no particular upper limit for the concentration of the copper citrate which can be administered to the poultry. However, large doses of copper citrate may be toxic to poultry and should therefore be avoided. Furthermore, greater amounts of copper citrate do not produce directly proportional weight gains. The copper citrate can be added to the poultry feed in amounts sufficient to enhance the weight gain of the poultry. Optimum concentrations of the copper titrate useful in the present invention are between approximately 50 ppm and 125 ppm copper metal equivalent; preferably approximately 63 ppm copper metal equivalent. These dosage rates can be achieved by dry blending between approximately 0.25 lbs and 0.62 lbs of copper citrate, preferably approximately 0.31 lbs of copper citrate, with one ton of poultry feed.

The following examples are illustrative of the present invention and are not intended to limit the scope of the invention as set forth in the appended claims. All temperatures are in degrees Celsius and all percentages are by weight unless specifically stated otherwise.

EXAMPLE 1

A total of 40 day old male broiler chickens were divided into five separate groups for testing. The first group, which served as a control, was fed a diet of ground yellow corn and soy bean meal without any copper citrate. The second group was fed a diet of ground yellow corn and soy bean meal mixed with copper citrate at the rate of 63 ppm copper (metal equivalent). The third group was fed a diet of ground yellow corn and soy bean meal mixed with copper citrate at the rate of 125 ppm copper metal equivalent. The fourth group was fed a diet of ground yellow corn and soy bean meal mixed with copper sulfate at the rate of 125 ppm copper metal equivalent. The fifth group was fed a diet of ground yellow corn and soy bean meal mixed with copper sulfate at the rate of 250 ppm copper metal equivalent. The amount of feed consumed by each group of chickens was weighed each day. The chickens in each group were weighed at 21 days, 35 days and 42 days. The results of the test are shown in Table 1 below.

TABLE 1

| Supplemental Copper (ppm) | Kg. Feed/Kg. Chicken Weight | | |
|---|---|---|---|
| | Control | Copper Citrate | Copper Sulfate |
| 21 Days: | | | |
| 0 | 1.749 | | |
| 63 | | 1.677 | |
| 125 | | 1.7 | 1.721 |
| 250 | | | 1.769 |
| Mean ± SE | 1.794 ± 0.04 | 1.700 ± 0.02 | 1.745 ± 0.01 |
| 35 Days: | | | |
| 0 | 1.871 | | |
| 63 | | 1.716 | |
| 125 | | 1.752 | 1.872 |
| 250 | | | 1.846 |
| Mean ± SE | 1.871 ± 0.07 | 1.734 ± 0.03 | 1.859 ± 0.02 |
| 42 Days: | | | |
| 0 | 2.000 | | |
| 63 | | 1.847 | |
| 125 | | 1.905 | 1.967 |
| 250 | | | 1.952 |
| Mean ± SE | 2.000 ± 0.07 | 1.889 ± 0.02 | 1.959 ± 0.01 |

As can be seen from the foregoing data, at the end of the test (day 42), the chickens which were treated with copper titrate consumed 70 grams less food than the chickens treated with the copper sulfate and 111 grams less food than the untreated chickens (control) per unit weight (per pound) of chicken.

EXAMPLE 2

The same procedure as Example 1 was followed. The results of this test are shown in Table 2 below.

TABLE 2

| Supplemental Copper (ppm) | Chicken Weight (Kg.) | | |
|---|---|---|---|
| | Control | Copper Citrate | Copper Sulfate |
| 21 Days: | | | |
| 0 | 0.682 | | |
| 63 | | 0.699 | |
| 125 | | 0.713 | |
| 250 | | | 0.709 |
| Mean ± SE | 0.682 ± 0.03 | 0.706 ± 0.01 | 0.709 ± 0.02 |
| 35 Days: | | | |
| 0 | 1.622 | | |
| 63 | | 1.770 | |
| 125 | | 1.691 | 1.657 |
| 250 | | | 1.624 |
| Mean ± SE | 1.622 ± 0.02 | 1.731 ± 0.03 | 1.640 ± 0.01 |
| 42 Days: | | | |
| 0 | 2.062 | | |
| 63 | | 2.217 | |
| 125 | | 2.155 | 2.148 |
| 250 | | | 2.101 |
| Mean ± SE | 2.062 ± 0.02 | 2.186 ± 0.01 | 2.125 ± 0.02 |

As can be seen from this data, at the end of the test (day 42), the chickens treated with the copper citrate weighed 61 grams more than the chickens treated with copper sulfate and 124 grams more than the chickens receiving no treatment (control).

It should be understood, of course, that the foregoing relates only to certain disclosed embodiments of the present invention and that numerous modifications or alterations may be made therein without departing from the spirit and scope of the invention as set forth in the appended claims.

What is claimed is:

1. A method of improving weight gain in a chicken comprising the step of:

administering orally to said chicken an effective amount of copper citrate and an amount of feed sufficient to produce weight gain in said chicken.

2. The method of claim 1, wherein said copper citrate is administered to said chicken by combining said copper citrate with said feed for said chicken.

3. The method of claim 2, wherein said copper citrate in said feed is present in an amount between approximately 50 ppm and 125 ppm copper metal equivalent.

4. The method of claim 2, wherein said copper citrate in said feed is present in an amount of approximately 63 ppm copper metal equivalent.

5. A composition for improving the weight gain and the food conversion efficiency of a chicken, said composition comprising:

a feed for said chicken; and an effective amount of copper citrate.

6. The composition of claim 5, wherein said copper citrate in said feed is present in an amount between approximately 50 ppm and 125 ppm copper metal equivalent.

7. The composition of claim 5, wherein said copper citrate in said feed is present in an amount of approximately 63 ppm copper metal equivalent.

8. The composition of claim 5, wherein said feed is selected from the group consisting of corn, soy beans and mixtures thereof.

9. The composition of claim 5, wherein said feed is selected from the group consisting of carbohydrates, barley; buckwheat; cassava; corn, yellow corn, white corn, high-lysine corn; millet molasses; oats; rice; rye; sorghums, kafir, milo; triticale; wheat; mill by-products, hominy feed; rice bran; rice hulls; wheat by-products, wheat bran, wheat millings, shorts; fats, oils, hard fats from slaughtered cattle; soft fats, yellow grease; hydrolyzed animal fats; vegetable oils; polyunsaturated fatty acids in egg yolks; proteins of animal origin, dried blood; dried poultry waste, dried cage layer manure; liver meal; meat by-products, meat scraps, meat and bone meal; milk products, dried skim milk; dried butter milk, dried whey; poultry by-products, hydrolyzed poultry feather meal; poultry hatchery by-product meal, eggshells, unhatched eggs, infertile eggs, culled chicks; proteins of fish origin, white fish meal; dark fish meal; shrimp meal; proteins of vegetable origin, corn gluten, coconut oil meal; cottonseed meal; guar meal; linseed oil meal; peanut (groundnut) meal; rapeseed oil meal; safflower meal; sesame meal; soybean meal; full-fat soybeans; sunflower seed meal; green leafy products, alfalfa products, sun-cured alfalfa meal, dehydrated alfalfa meal, dehydrated alfalfa leaf meal and mixtures thereof.

10. A method of improving feed conversion efficiency in a chicken comprising the step of:

administering orally to said chicken an effective amount of copper citrate and an amount of feed sufficient to produce weight gain in said chicken.

11. The method of claim 10, wherein said copper citrate is administered to said chicken by combining said copper citrate with said feed for said chicken.

12. The method of claim 11, wherein said copper citrate in said feed is present in an amount between approximately 50 ppm and 125 ppm copper metal equivalent.

13. The method of claim 11, wherein said copper citrate in said feed is present in an amount of approximately 63 ppm copper metal equivalent.

* * * * *